United States Patent [19]
Yamaguchi et al.

[11] Patent Number: 5,246,700
[45] Date of Patent: Sep. 21, 1993

[54] PHARMACEUTICAL COMPOSITIONS FOR TREATING BONE DISORDERS

[75] Inventors: Ken Yamaguchi; Koichi Nagasaki, both of Tokyo; Sumiya Eto, Kitakyushu, all of Japan

[73] Assignee: Tonen Corporation, Tokyo, Japan

[21] Appl. No.: 791,386

[22] Filed: Nov. 14, 1991

[30] Foreign Application Priority Data

Jun. 19, 1991 [JP] Japan ................................. 3-173355

[51] Int. Cl.$^5$ ....................... C07K 15/26; C07K 13/00
[52] U.S. Cl. ................................. 424/85.2; 424/85.1; 530/351
[58] Field of Search ............................ 424/85.1, 85.2; 530/351

[56] References Cited

U.S. PATENT DOCUMENTS

| | | | |
|---|---|---|---|
| 4,863,726 | 9/1989 | Stevens et al. | 424/85.1 |
| 5,013,824 | 5/1991 | Abrams et al. | 530/351 |
| 5,017,691 | 5/1991 | Lee et al. | 424/85.2 |

*Primary Examiner*—Howard E. Schain
*Assistant Examiner*—P. Lynn Touzeau
*Attorney, Agent, or Firm*—Bacon & Thomas

[57] ABSTRACT

A composition for treating bone disorder or hypercalcemia of patients suffering from malignant tumors is disclosed. The composition of the present invention comprises an effective amount of interleukin-4 in a pharmaceutically acceptable carrier.

6 Claims, 2 Drawing Sheets

PHARMACEUTICAL COMPOSITIONS FOR TREATING BONE DISORDERS

BACKGROUND OF THE INVENTION

I. Field of the Invention

The present invention relates to a pharmaceutical composition for treating bone disorders such as osteoporosis or hypercalcemia of patients suffering from malignant tumors. The present invention also relates to methods for treating these diseases.

II. Description of the Related Art

Osseous tissue is composed of collagen, organic components fulfilling the clearances among the collagen, and bone matrix consisting of inorganic components comprising calcium and phosphorus as major constituents. Bones are continuously renewed by periodically repeating the osteogenesis by osteoblasts and the bone resorption by osteoclasts. Mechanical stimulations, various hormones, topical factors and the like influence the bone metabolism and the amount of the bone salt is maintained at about a certain level based on the balance of these factors. The representative bone disorder caused by the loss of this balance is osteoporosis. Osteoporosis is a systemic metabolic bone disorder which causes the decrease in the amount of the bones without associating chemical change of the bones, and in turn, adverse change of dynamic structure of the bones so as to show symptoms such as fracture of lumbar vertebra and femur, as well as pain in the waist and back.

On the other hand, bones are also important for the homeostasis of minerals. As a dysbolism of calcium, hypercalcemia accompanied by malignant tumors is known. Since the hypercalcemia is partly caused by the humoral factor produced by the tumor, the hypercalcemia is called humoral hypercalcemia of malignancy (HHM). Most of HHM shows hypercalcemia, hypophosphatemia, high level of CAMP in urine, reduction of threshold value of resorption of phosphate by renal tubule and the like, and presents symptoms including digestive disorders such as nausea and vomiting, and central nervous disorders such as easy feeling of fatigue, confusion and coma. The disorder rapidly proceeds and the symptoms are heavy.

As the substance causing the disorder, parathyroid hormone related protein (PTHrP) was recently isolated. This protein consists of 141 amino acids and has an amino acid sequence at its N-terminal region similar to that of parathyroid hormone (PTH).

Osteoclast activating factor (OAF) is also considered as a substance causing HHM. OAF is now considered identical with interleukin-1. Other known substances which promote the bone resorption include TNF-α, TNF-β and TGF-α.

The treatment of HHM is basically carried out by co-employment of sufficient supplementation of fluid and Flomide (ectaric acid), and additionally, administration of calcitonin, glucocorticoid, indomethacin, mysramicin or the like is necessary. However, the therapeutic effect is small even if any of these methods is employed since the therapeutic effect is only temporary or the side effect must be taken into consideration.

The conventional treatment of osteoporosis is based on the promotion of osteogenesis and inhibition of bone resorption. Particularly, calcium formulations, estrogen, active vitamin D, calcitonin, Ipriflavon, bisphosphate are conventionally used for the treatment of osteoporosis. However, none of these is an effective therapeutic agent.

SUMMARY OF THE INVENTION

Accordingly, an object of the present invention is to provide a pharmaceutical composition for treating bone disorders caused by dysbolism of calcium represented by hypercalcemia.

Another object of the present invention is to provide a pharmaceutical composition for treating hypercalcemia accompanied by malignant tumors.

The present inventors intensively studied to first find that interleukin-4 which is a cytokine inhibits the bone resorption. Further, the present inventors actually succeeded in reducing the calcium level in blood of mice suffering from hypercalcemia to the normal level, thereby completing the present invention.

That is, the present invention provides a pharmaceutical composition for treating bone disorders comprising an effective amount of interleukin-4 in a pharmaccutically acceptable carrier.

The present invention also provides a pharmaceutical composition for treating hypercalcemia of a patient suffering from a malignant tumor, comprising an effective amount of interleukin-4 in a pharmaceutically acceptable carrier.

The present invention further provides a method for treating bone disorders, comprising administering an effective amount of interleukin-4 to a patient suffering from a bone disorder.

The present invention still further provides a method for treating hypercalcemia of a patient suffering from a malignant tumor, comprising administering an effective amount of interleukin-4 to said patient.

By the present invention, a novel pharmaceutical composition effective for the treatment of bone disorders caused by dysbolism of calcium and for the treatment of hypercalcomia of patients suffering from malignant tumor, which pharmaceutical composition does not substantially show side effects. No pharmaceutical is known which can reduce the calcium level in blood and can maintain the reduced the calcium level in blood and can maintain the reduced calcium level for a long time, and which does not have side effects. The pharmaceutical composition of the present invention can restore the calcium level in blood to the normal level significantly more effectively than the conventional therapeutic agents such as calcitonin, glucocorticoid, indomethacin, mysramicin and the like.

DETAILED DESCRIPTION OF THE PREFERRED EMBODIMENTS

Figure 1:
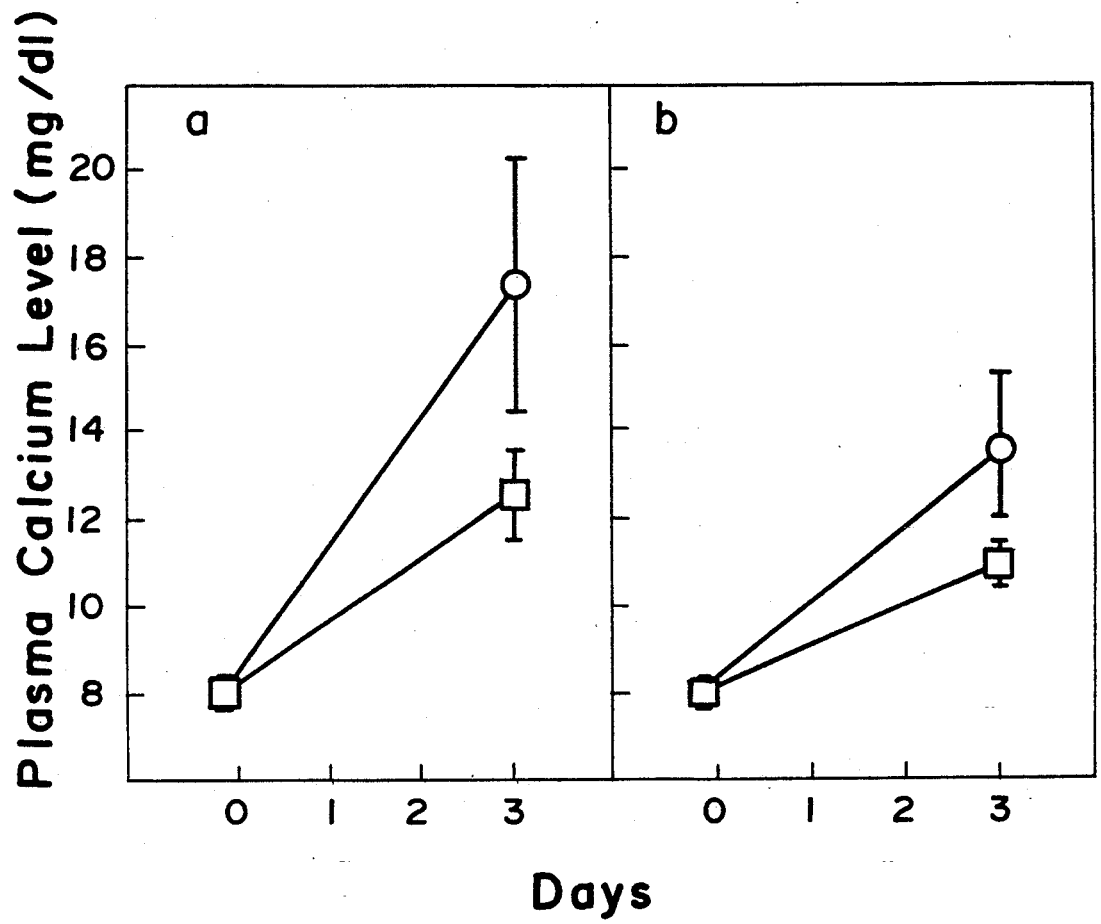
FIG. 1 shows the effectiveness of interleukin-4 in nude mice to which PTHrP was continuously administered.

Interleukin-4 is a known substance and has been cloned by Severison et al from cDNA prepared from a ConA-stimulated mouse T cell line. The mouse interleukin-4 is a protein consisting of 120 amino acids. The structure of human interleukin-4 was also determined by Yokota et al, which is a protein consisting of 129 amino acids. It has been reported that both of the mouse and human interleukin-4 contain two sugar chain-binding sites.

Interleukin-4 is known to have the following physiological activities:

1) As can be seen from that fact that interleukin-4 was originally reported as B lymphocytes growth factor, it induces DNA synthesis of B lymphocytes activated by an antigen or an anti-IgM antibody, and promotes the growth of B lymphocytes.
2) It selectively differentiates B cells stimulated by lipopolysaccharides (LPS) to IgG1-producing cells so as to reduce the production of IgG3. It is also known that it promotes the production of IgE.
3) It induces the expression of Class TT major histocompatibility antigen (Ia antigen).
4) It promotes growth of T cells.
5) It promotes growth of mastocytes.
6) It promotes growth and differentiation of thymue cells.
7) It expresses the Fce receptor.
8) It promotes growth of hematopoietic stem cells.

Thus, it is known that interleukin-4 has a wide variety of physiological activities. Especially, it has been emphasized that interleukin-4 plays important roles in promoting the humoral immune response. However, it is not known that interleukin-4 has an effect to reduce the bone resorption.

As will be concretely described in the actual working examples described below, the present inventors first showed the effectiveness of interleukin-4 for the treatment of hypercalcemia using two different animal study systems. In one animal study, it was shown that interleukin-4 has an effect to reduce the rise of calcium level in blood in nude mice to which PTHrP that is a hypercalcemia-inducing factor is continuously administered. In another animal study, it was shown that the calcium level in blood of nude mice having hypercalcemia prepared by transplanting thereto a PTHrP-producing tumor was restored to the normal level. From these results, it was proved that interleukin-4 reduces the bone resorption in the dysbolism of calcium represented by hypercalcemia, and so is effective for the therapy of bone disorders.

The pharmaceutical composition of the present invention comprises interleukin-4 as an effective ingredient in an amount effective for the treatment of bone disorders or hypercalcemia accompanied by malignant tumors. The pharmaceutical composition of the present invention may be administered to human in an amount of about 10 μg/kg/day to about 1 mg/kg/day in terms of the weight of interleukin-4.

The pharmaceutical composition of the present invention may preferably be administered by intravenous injection or intramuscular injection, or by embedding an osmotic minipump containing the composition in the body so as to attain continuous administration.

The pharmaceutical composition may be prepared by formulating interleukin-4 with any one or more pharmaceutically acceptable carriers well-known in the art. For example, the pharmaceutical composition may have a formulation, for example, comprising $1 \times 10^{-7}$M to $1 \times 10^{-3}$M of interleukin-4 in physiological saline or in a citrate buffer containing a small amount of albumin as a stabilizer.

The pharmaceutical composition of the present invention is effective for the therapy of various bone diseases such as osteoporosis in which abnormal metabolism of calcium occurs, and for the therapy of hypercalcemia accompanied by malignant tumors.

The present invention will now be described by way of examples thereof. It should be noted, however, the examples are presented for the illustration purpose only and should not be interpreted in any restrictive way.

EXAMPLE 1

Effectiveness of Interleukin-4 in Nude Mice to Which PTHrP was Continuously Administered In both sides of abdominal cavities of nude mice, osmotic minipumps containing compositions were embedded so as to continuously administer the compositions to the nude mice. Three days after the commencement of the continuous administration, the calcium level in blood was determined. The nude mice were grouped into the following four groups and each group received the following composition:

Group 1: physiological saline containing 600 pmol/day of PTHrP (1st–34th amino acid) and 0.1 wt % of BSA Group 2: physiological saline containing 600 pmol/day of PTHrP (1st–34th amino acid), 5 μg/day (350 pmol/day) of mouse interleukin-4 and 0.1 wt % of BSA Group 3: physiological saline containing 600 pmol/day of PTHrP (1st to 141st amino acid) and 0.1 wt % of BSA Group 4: physiological saline containing 600 pmol/day of PTHrP (1st–141th amino acid), 5 μg/day (350 pmol/day) of mouse interleukin-4 and 0.1 wt % of BSA The results are shown in FIG. 4. In FIG. 1, the symbol "◯" in "a" shows the results of Group 1, the symbol □ in "a" shows the results of Group 2, the symbol "◯" in "b" shows the results of Group 3, and the symbol □ in "b" shows the results of Group 4. As can be seen from FIG. 1, in Group 1 to which only PTHrP (1st–34th amino acid) was administered, drastic rise of calcium level in blood was observed while the calcium level in blood of Group 2 to which interleukin-4 was administered along with PTHrP, significant reduction of the calcium level was observed. The similar effect was observed on the system in which PTHrP (1st–141st amino acid) was administered.

EXAMPLE 2

Human lung cancer cell lines Lu-61 and Lu-65A which are known to produce PTHrP were transplanted to nude mice. After two months from the transplantation, nude mice having tumor weight of more than 1.5 g and exhibiting advanced hypercalcemia were obtained. Three mice of which calcium level exceeded 10.5 mg/dl were selected and interleukin-4 was continuously administered at a dose of 5 μg/day by using osmotic minipumps. After three days from the beginning of the administration, calcium level in blood was measured.

Figure 2:
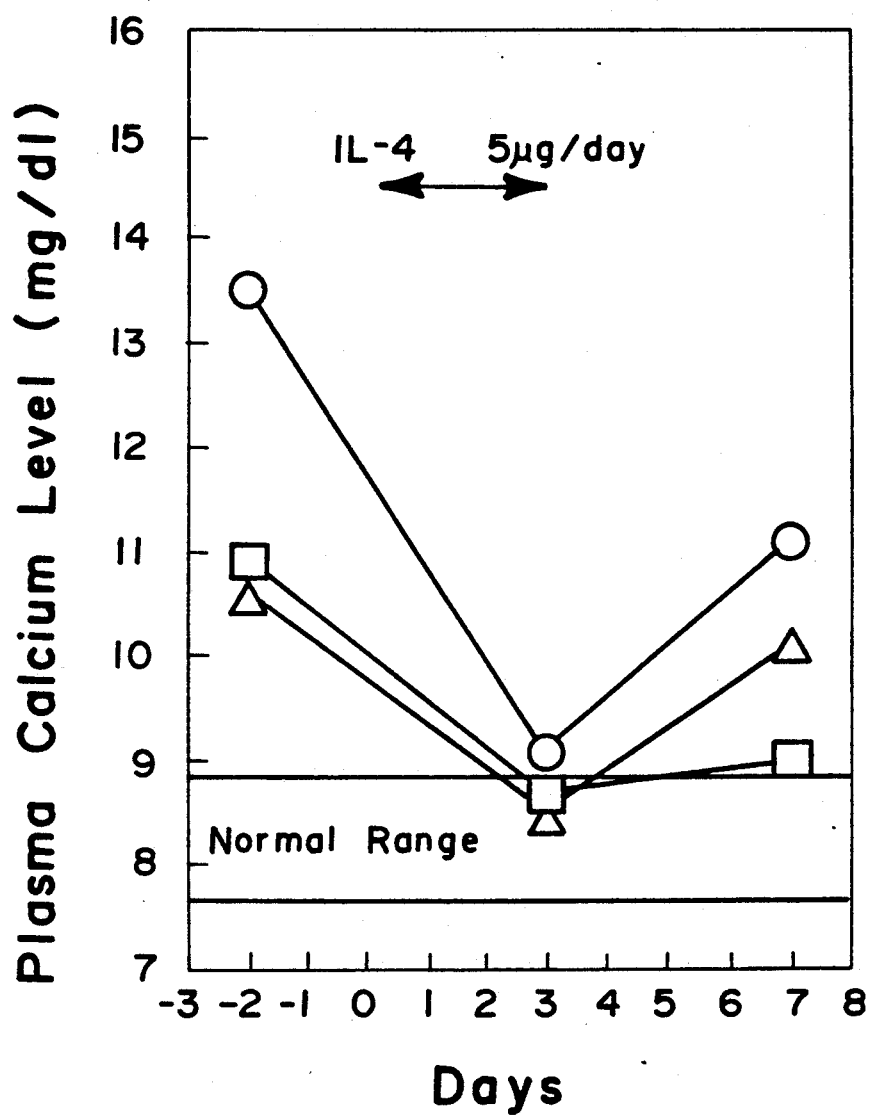
FIG. 2 shows the effectiveness of interleukin-4 in mice to which PTHrP-producing tumor was transplanted.

The results are shown in FIG. 2. In FIG. 2, the symbols ◯ and Δ show the results of Lu-61 and the symbol □ shows the results of Lu-65A. As can be seen from FIG. 2, the calcium level in blood of normal mice is about 8 mg/dl while it was as high as 11–14 mg/dl in the mice to which the human lung cancer cell lines were transplanted. However, after three days from the beginning of the continuous administration of interleukin-4, the calcium level was almost restored to the normal level. After stopping the continuous administration of interleukin-4, the calcium level in blood rose again.

We claim:

1. A method for the treatment of a patient suffering from a bone disorder caused by dysbolism of calcium, comprising administering to said patient an effective amount to treat the bone disorder of interleukin-4.

2. A method according to claim 1 wherein the bone disorder is osteoporosis.

3. A method for the treatment of a patient suffering from hypercalcemia accompanied by a malignant tumor, comprising administering to said patient an effective amount to treat hypercalcemia of interleukin-4.

4. A method according to claim 1 wherein the effective amount is from about 10 μg/kg to 1 mg/kg per day by weight of interleukin-4.

5. A method according to claim 2 wherein the effective amount is from about 10 μg/kg to 1 mg/kg per day by weight of interleukin-4.

6. A method according to claim 3 wherein the effective amount is from about 10 μg/kg to 1 mg/kg per day by weight of interleukin-4.

* * * * *